June 30, 1942. J. N. MEADOWCROFT, SR Plant Pat. 530
ROSE PLANT
Filed Jan. 9, 1942
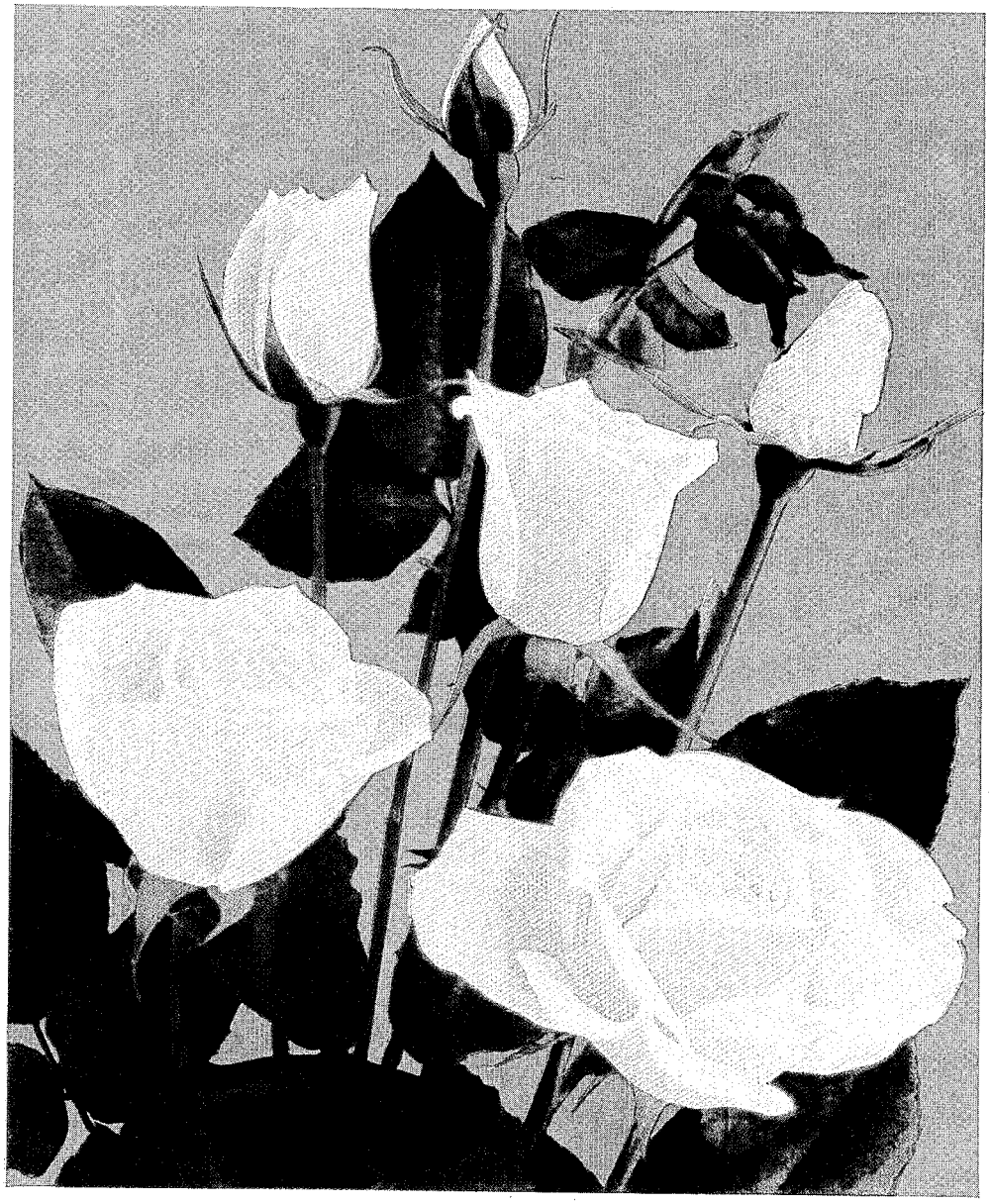
Inventor
James N. Meadowcroft, Sr.
By Robert Robb
Attorneys Patented June 30, 1942

Plant Pat. 530

UNITED STATES PATENT OFFICE

530

ROSE PLANT

James N. Meadowcroft, Sr., Kennett Square, Pa., assignor to J. H. Thompson's Sons, Kennett Square, Pa.

Application January 9, 1942, Serial No. 426,232

1 Claim. (Cl. 47—61)

This invention relates to a new and distinct variety of rose plant having as its objective the improvement in the hybrid tea class of roses useful both for cut flowers and garden decoration purposes.

To this end, I crossed an unnamed seedling with the well known variety "Souvenir," with the result that there was produced a rose possessed of an unusual combination of qualities, the superiority of which over others of the same class, lying particularly in the form and size of the flower, the long lasting quality of the blooms on the bush and when cut, the combination coloring of the blooms and the strong habits of growth, as hereinafter more specifically set forth.

The following is a detailed description of this new rose, the color terminology employed being in accordance with Ridgway's Color Standard:

Type: Hardy; tall bush; greenhouse; outdoors; seedling; for cut flowers and garden decoration.
Class: Hybrid tea.
Parentage: Seedling.
*Seed parent.*—Unnamed seedling.
*Pollen parent.*—"Souvenir" (Plant Patent No. 25).
Propagation: Holds its distinguishing characteristics through succeeding propagations by grafting and budding.

*Flower*

Locality where grown: Kennett Square, Pennsylvania.
Flowers borne: Singly to stem, on strong, long stems.
Quantity of bloom: Abundant outdoors and in greenhouse.
Continuity: Continuous.
Fragrance: Slight; Sweetbriar.
Bud:
*Peduncle.*—Long; medium heavy; erect; stiff; Scheele's Green, Plate 6; entirely smooth.
*Before calyx breaks.*—*Size*—medium. *Form*—long; pointed with a conspicuous neck; with foliaceous parts extending beyond the tip of the bud equal to one-fourth of its length.
*As calyx breaks.*—Light Orange Yellow, Plate 3.
*As first petal opens.*—*Size*—medium. *Form*—ovoid. *Color:* Outside—Light Orange Yellow, Plate 3; inside—Pale Orange Yellow, Plate 3. *Opening*—opens up well.
Bloom:
*Size, when fully open.*—Large; five inches to five and a half inches.
*Petalage.*—Double; from twenty-five to thirty petals arranged regularly.
*Form.*—Cupped; petals remaining at first tightly cupped, rolled outward; becoming later, at maturity, loosely cupped, rolled outward.
Petals: Thick; leathery; with inside and outside satiny.
*Shape.*—Outside—obovate. Intermediate—obovate. Inside—obovate.

This description of a newly opened flower was made from a rose grown in a greenhouse, in December, 1941, at Kennett Square, Pennsylvania:

*Color.*—Outside petal: outside surface—Light Orange Yellow, Plate 3; inside surface—Pale Orange Yellow, Plate 3. Intermediate petal: outside surface—Light Orange Yellow, Plate 3; inside surface—Pale Orange Yellow, Plate 3. Inner petal: outside surface—Light Orange Yellow, Plate 3; inside surface—Pale Orange Yellow, Plate 3.

This description was made from a rose that was open for three days in a greenhouse, in December 1941, at Kennett Square, Pennsylvania:

*Color.*—Outside petal: outside surface—Maize Yellow, Plate 4; inside surface—Pale Ochraceous Salmon, Plate 15. Inside petal: outside surface—Maize Yellow, Plate 4; inside surface—Pale Ochraceous Salmon, Plate 15.
*General color effect.*—Newly opened flower—Orange Buff, Plate 3. Three days open—Pale to Light Buff, Plate 15.
*Behavior.*—Drop off cleanly.
*Flower longevity.*—Cut roses grown in greenhouse kept at living room temperatures five to seven days.

*Reproductive organs*

Stamens: Many; arranged regularly.
Filaments: Medium length; Scarlet Red, Plate I; most with anthers.
Anthers: Medium size; Capucine Yellow, Plate 3; open at once and at various times.
Pollen: Abundant; Orange, Plate 3.
Pistils: Many.
Styles: Even; medium length; columnar.
Stigma: Light Buff, Plate 15.
Ovaries: All enclosed in calyx.

Hips: Apple Green, Plate 17; with neck pear-shaped; walls thin, fleshy.
Sepals: Long; spear-shaped; recurved.
Seeds: Many; medium size.

*Plant*

Foliage:

*Leaves.*—Compound of five to seven leaflets; abundant; large; leathery; glossy.

*Leaflets.*—Shape—Ovoid, with apex acute; base round; margin simply serrate.

*Color.*—*Mature:* upper surface—Elm Green, Plate 17; under surface—Light Bice Green, Plate 17. *Young:* upper surface—Serpentine Green, Plate 16; under surface—Sudan Brown, Plate 3.

*Rachis.*—Medium heavy. Upper side—smooth; grooved. Under side—smooth.

*Stipules.*—Medium length; medium wide; with medium long points turning out at an angle of more than 45°, recurved toward the stem.

*Disease.*—Resistant to mildew and blackspot.

Growth:

*Habit.*—Upright; much branched.

*Growth.*—Free; vigorous.

*Canes.*—Heavy.

*Main Stems.*—Elm Green, Plate 17. *Thorns*—several; short; hooked downward; with narrow base. *Prickles*—none. *Hairs*—none.

*Branches.*—Biscay Green, Plate 17. *Thorns*—few; short; hooked downward; with narrow base. *Prickles*—none. *Hairs*—none.

*New Shoots.*—Biscay Green, Plate 17. *Thorns*—few; hooked downward; with narrow base. *Prickles*—none. *Hairs*—none.

I claim:

A new and distinct variety of hybrid tea rose plant, characterized as to novelty by its strong habits of growth, lasting quality of its blooms, large size and cupped form of its flowers, and the color combination of said flowers, substantially as shown and described.

JAMES N. MEADOWCROFT, SR.